US010449120B2

(12) United States Patent
Govindasamy et al.

(10) Patent No.: US 10,449,120 B2
(45) Date of Patent: Oct. 22, 2019

(54) SYSTEM FOR AUTHORIZED DISPENSING OF MEDICINES

(71) Applicants:Murugesan Govindasamy, Chandler, AZ (US); Cassie Sleppy, Greenville, OH (US)

(72) Inventors: Murugesan Govindasamy, Chandler, AZ (US); Cassie Sleppy, Greenville, OH (US)

( * ) Notice: Subject to any disclaimer, the term of this patent is extended or adjusted under 35 U.S.C. 154(b) by 0 days.

(21) Appl. No.: 16/282,963

(22) Filed: Feb. 22, 2019

(65) Prior Publication Data

US 2019/0183739 A1    Jun. 20, 2019

Related U.S. Application Data

(62) Division of application No. 15/180,591, filed on Jun. 13, 2016.

(Continued)

(51) Int. Cl.
*A61J 7/00*        (2006.01)
*A61J 7/04*        (2006.01)
(Continued)

(52) U.S. Cl.
CPC .......... *A61J 7/0436* (2015.05); *A61J 7/0084* (2013.01); *A61M 5/20* (2013.01); *A61M 5/31586* (2013.01); *A61M 5/5086* (2013.01); *G16H 20/17* (2018.01); *A61J 2200/30* (2013.01); *A61J 2200/70* (2013.01); *A61M 2005/2006* (2013.01); *A61M 2005/31588* (2013.01); *A61M 2205/18* (2013.01); *A61M 2205/27* (2013.01); *A61M 2205/3584* (2013.01);
(Continued)

(58) Field of Classification Search
None
See application file for complete search history.

(56) References Cited

U.S. PATENT DOCUMENTS

| 4,465,191 A | | 8/1984 | Darbo |
| 4,563,175 A | * | 1/1986 | LaFond ............... A61M 5/1456 128/DIG. 12 |

(Continued)

FOREIGN PATENT DOCUMENTS

WO        0063857 A1    10/2000

*Primary Examiner* — Timothy R Waggoner
(74) *Attorney, Agent, or Firm* — Jacob M. Ward; Ward Law Office LLC

(57) ABSTRACT

A portable compact scaled-down programmable system for authorized dispensing of medicines is illustrated. The system includes at least one enclosure, a dispenser unit having an integrated cap and a plurality of dispensing slots, adapted to facilitate dispense of at least one medicine to an authentic user. The system further includes a driving mechanism for the upward and downward movement of the dispenser unit, a control unit to facilitate controlled functioning of functional units of the system, a primary sensor unit to facilitate the identification and authorization, a power supply unit, a micro-USB, a GNSS module, a set of status indicators having a liquid crystal display, a speaker, a vibrator and a LED, a set of knobs, and a communication facilitator. Further, the system can be operated either in stand-alone mode and or in paired mode. The system is configured to include a plurality of internet of things [IoT] modules.

5 Claims, 12 Drawing Sheets

Related U.S. Application Data

(60) Provisional application No. 62/183,913, filed on Jun. 24, 2015.

(51) Int. Cl.
*A61M 5/50* (2006.01)
*A61M 5/315* (2006.01)
*G16H 20/17* (2018.01)
*A61M 5/20* (2006.01)

(52) U.S. Cl.
CPC ... *A61M 2205/502* (2013.01); *A61M 2205/52* (2013.01); *A61M 2205/581* (2013.01); *A61M 2205/582* (2013.01); *A61M 2205/583* (2013.01); *A61M 2205/587* (2013.01); *A61M 2205/609* (2013.01); *A61M 2205/8206* (2013.01)

(56) References Cited

U.S. PATENT DOCUMENTS

| | | |
|---|---|---|
| 6,109,774 A | 8/2000 | Holmes et al. |
| 6,662,081 B1 | 12/2003 | Jacober et al. |
| 7,359,765 B2 | 4/2008 | Varvarelis et al. |
| 8,905,964 B2 * | 12/2014 | Poutiatine ............. A61J 7/0038 604/59 |
| 9,072,652 B1 | 7/2015 | Balasubramanian et al. |
| 2012/0160716 A1 | 6/2012 | Chan et al. |
| 2013/0134180 A1 | 5/2013 | Cheyene |
| 2013/0184676 A1 * | 7/2013 | Kamen ............. A61M 5/14216 604/506 |
| 2015/0257979 A1 * | 9/2015 | Jenema ................. A61J 7/0053 604/516 |
| 2016/0042150 A1 | 2/2016 | Moloughney |
| 2017/0326034 A1 | 11/2017 | Lewis |

\* cited by examiner

SYSTEM FOR AUTHORIZED DISPENSING OF MEDICINES

CROSS-REFERENCE TO RELATED APPLICATIONS

The present divisional patent application and the specification thereof is in reference to and claims the benefit of the U.S. patent application Ser. No. 15/180,591, filed on Jun. 13, 2016, which in turn claims priority to the U.S. provisional patent application Ser. No. 62/183,913 in accordance with 35 U.S.C. § 119(e), entitled 'A SYSTEM FOR AUTHORIZED DISPENSING OF MEDICINES' and filed before the Honourable Commissioner of Patents, United States Patent and Trademark Office, on the 24th day of June, 2015.

FIELD

The present invention relates to a dispensing system generally, and in particular to a system for authorized dispense of medicines to an individual at pre-defined and pre-programmed time to ensure proper dosage of medicines, to prevent over dosage of medicines and the omission of prescribed medication, and drug abuse.

BACKGROUND

Medicines play a vital role in patients and healthcare industry. In the traditional system of medication, a physician looks into the symptoms of the illness in a patient and decides the kind, quality and the quantity of the medicine to be delivered to make the patient recuperate from the illness. The decision of the physician is communicated to a pharmacist in writing and the pharmacist holds the responsibility to dispense the right medicine comprising suitable medicinal formulation. The medicinal formulation included in a medicine may be either in the solid form that includes tablets, pills, finely granulated powders, injectable and the like or in the liquid form like syrups, and tonics or in gaseous form like sprays. Sometimes, the formulation may be a gel, paste or cream like ointments.

The delivery of right medicine to a particular illness depends on a plurality of factors. These factors include age, sex, weight, height and severity of illness, in addition to various other physical factors including blood pressure, sugar level in the body and in the blood. Sometimes, a medicine delivered for one kind of illness may be in severe contradiction to another kind of illness in the same patient.

Referring to the prior art, a study by American researchers shows that nearly seventy percent of Americans take prescription drugs, and more than half the US people receive at least two prescriptions. Twenty percent of US patients are found to be on five or more prescription medications. Among these prescriptions, antibiotics, antidepressants and painkiller opioids are the most common ones.

Expenditure on prescription drugs in the US accounts for more than for 12% of total personal health care expenditures. Many types of prescription drugs are abused. If a medicine is taken in a way that is different from what a physician has prescribed, then it is considered as prescription drug abuse. The prescription drug abuse may be due to any or all of the following reasons:

- taking a medicine that was prescribed for someone else;
- taking a larger dose of the prescribed medicine than prescribed dosage;
- taking the prescribed medicine in a way different from the way as prescribed by the physician; and
- using the prescribed medicine for another purpose.

Abusing some prescription drugs can lead to addiction including addiction to narcotic painkillers, sedatives, tranquilizers, and stimulants.

In US, it is estimated that nearly three fourth of prescription drug overdoses are caused by prescription painkillers alone. These prescription painkillers are also known as opioid pain relievers. Many people use prescription painkillers non-medically. Death due to the prescription drug overdoses is more than the deaths due to cocaine and heroin combined. Most of these drug overdose deaths are caused due to prescription drugs.

It has been observed that prescription drugs come from hospitals and emergency rooms, clinics, and pharmacies. Instead of meeting with a dealer, drugs could be made readily available by a physician by a simple prescription.

Nowadays, as more and more people are depending on medicines, manual dispensing of medicines has become a cumbersome task for pharmacists. In many cases, there is a risk of giving medicines without proper prescription by a physician. Hence, systems for dispensing medicines have been developed. The medicine dispensing systems available at present are bulky. It makes people unable to carry the dispensing system with them.

Further, in the aforementioned traditional medicine dispensing systems, there is no control over both the usage and misuse of medicines. Also, many of these aforementioned traditional systems are devoid of authorized dispensing of required medicines.

The United States patent application filed by Joseph Moloughney (Pompton Plaines, N.J., US), bearing the application Ser. No. 14/456,172 and publication No. US20160042150, and entitled 'Intelligent Pill Dispenser With Remote Scheduling and Monitoring', discloses a medication dispensing system with a remote app or a web page that allows an end user or a remote caregiver to create and change a dose per medication as well as a schedule for each medication dose. Further, the webpage is enabled to provide alerts and notifications, store history of doses delivered, and doses removed, and submit automatic refill requests when medication approach refill levels. In addition, the system in the aforementioned United States Patent document includes a medication dispense device having a plurality of medication storage containers, each such container configured to store one medication therein. A dispensing cup and one motor assembly to deliver the medication from the storage container are also provided in the system. Further, one physical control mechanism to warrant the accuracy of the dosage and a user interface to allow the end user to create and change a dose per medication as well as a schedule for each medication dose is provided. Additionally, a circuit board connected to the motor assembly and physical control mechanism is adapted to store software program as a logic of the device to control motors, to accept inputs from the physical control mechanism, from user interface, and inputs from the remote app or web page is provided. However, the drawback of the invention as described in the aforementioned US Patent document is that the device is not tamperproof and is deprived of the portability and authorization features.

The United States patent issued to Innovation Associates, Inc. (Johnson City, N.Y., US), bearing the application Ser. No. 13/853,230 and U.S. Pat. No. 9,072,652, and entitled 'Pill Counting and Dispensing Apparatus with Self-Calibrating Dispenser', discloses a self-contained pill dispenser. The pill dispenser, in accordance with the invention as disclosed in the aforementioned US Patent document comprises a housing enabled to support a hopper for containing a plurality of pills. There is a transport tube receives pills from the hopper. The transport tube has a controllable aperture to facilitate or to inhibit the delivery of the pills to the transport tube. There is a microcontroller functionally coupled with the hopper, the transport tube, and the input aperture. In addition, a feed chute is optionally coupled to the hopper and the transport tube. The system is enabled with a self-calibration of the mechanism for counting and dispensing pills by dynamically adjusting the input aperture based upon the stored information representative of the pulse width signal and the amplitude signal. However, the drawbacks associated with the system disclosed in aforementioned US patent document lies in that the device disclosed therein is not tamper-proof and is deprived of authorization and portability features. Further, the functioning of the system is complex.

A tamper-proof device for pill dispensing named Med Vault pill dispenser created by a group of students from Brigham Young University, is undergoing testing and is patent pending. The device, which is not commercially available in the market yet, enables a user to store the pills and dispense them at a set time. Further, the pharmacist of the user is required to enable the software program of the device, at the time of refilling, in order to determine the kind or type of pills to be dispensed and the time of dispensing. Additionally, a user is required to enter an access code on the top of the device, before a medication is dispensed on time. However, the system disclosed in the aforementioned Medvault pill dispenser developed by Brigham Young University is deprived of tracking mechanism for the proper dosage of medication. Further, the system is unable to dispense a plurality of medicines. Still further, the system is bulky.

The United States patent application filed by Shaahin Cheyene (Venice, Calif., US), bearing the application Ser. No. 13/308,493 and publication No. US20130134180, and entitled 'Digital Pill Dispenser', discloses a device for storing and dispensing pills and supplements of various kinds. The dispensed substance includes food, drug, supplements, liquids, powders or pills. The device consists of a rectangular body with rounded edges and display unit, the display unit further adapted to function as an alarm clock. The device may work with blister-packed pills or alternatively use an encapsulated compartment to hold and dispense loose pills. The device has an opening in the front and back so that the pills can be distributed. The device beeps, vibrates and illuminates to remind the user to take their pills or medicine in regular intervals. However, the system as disclosed in the aforementioned US Patent document lacks the technical features of authorization and tracking. Further, there is no mention of overdose prevention feature.

The PCT application filed by Kenneth Stillwell [US], bearing the international application No. PCT/US2000/009328 and the WIPO publication No. WO/2000/063857, and entitled 'Automatic Pill Dispenser', discloses a device and a method thereon for dispensing pills or vitamins. The device includes a rotatable chamber within a housing, the rotatable chamber further containing multiple slots for storing the pills or vitamins. The housing has at least one dispensing hole to facilitate the falling of pills from the containment slot, when the slot is aligned with the hole. The chamber may be rotated preferably by motorization. However, the rotation by manual means is also allowed. The motorization contains an electric motor connected to a worm drive that engages gear teeth along the edge of the chamber. However, the drawbacks associated with the system disclosed in aforementioned PCT application lie in that the system disclosed therein is deprived of authorization feature.

The United States patent issued to Nicholas M. Varvarelis (3501 Conshokocken Avenue, Philadelphia, Pa., US) and Joshua Samuelson (126 Crum Creek Dr., Woodlyn, Pa., US) bearing the application Ser. No. 11/225,193 and U.S. Pat. No. 7,359,765, and entitled 'Electronic Pill Dispenser', discloses an electronic pill dispenser that includes a container and a cap that detachably attached to the container. Further components of the pill dispenser include a power source, pill dispenser circuitry, a real time clock, a counter, a display, a dispensing mechanism, a sensor, a visual indicator, an audible indicator, an input/output interface, an input output port, and a communication bus electrically interconnecting the components. The electronic pill dispenser may also include a physical indicator, a locking mechanism, a transceiver, an antenna, and a modem. The pill dispenser enhances patient compliance for following through a particular drug regimen by offsetting negative effects of memory loss and other cognitive dysfunctions, attenuation of special senses, poor eyesight, lack of patient education, etc. The pill dispenser is enabled to help the mentally unstable too. The electronic pill dispenser is configured to remind the users and dispense the pills to authorized individuals at appropriate times and is economical and convenient. However, the drawbacks associated with the system disclosed in aforementioned US patent document are that the device is unable to dispense a plurality of medicines and further the system is bulky.

None of the aforementioned prior art taken either singly or in combination, is seen to describe the present invention as claimed. Therefore, to overcome the drawbacks associated with the prior art, there is strong felt a need for a medicine dispensing system that:
   is tamper proof;
   is portable;
   is compact;
   is scaled-down in size
   enables dispensing of medicines with a control over the usage and misuse of medicines;
   provides for dispensing pre-determined set of medicines at pre-determined time intervals;
   prevents the omission of the prescribed medication with respect to people suffering from mental health;
   provides for authorized dispensing of medicines.

OBJECTS OF THE INVENTION

Few of the objects of the present invention are as stated below:
   An object of the present invention is to provide a tamper proof medicine dispensing system;
   Additional object of the present invention is to provide a portable medicine dispensing system;
   Another object of the present invention is to provide a system that facilitates a user with controlled dispensing of medicines;
   Additional object of the present invention is to provide a system that facilitates control over misuse of medicines;
   Another object of the present invention is to provide a system that enables authorized dispensing of medicines;
   Further object of the present invention is to provide a system that enables dispensing pre-determined set of medicines at pre-determined time intervals;

Additional object of the present invention is to provide a system that prevents the omission of the prescribed medication with respect to people suffering from mental health; and Yet another object of the present invention is to provide a system that facilitates a medical professional including a physician or a pharmacist with the usage data that is further processed for exploratory data analysis and extended patient drug use analysis.

These and other goals, objects, inventive features and advantages of the present invention, as defined solely by claims, will better understood by the following non-limiting detailed description taken in conjunction with the accompanying drawings.

SUMMARY OF THE INVENTION

A system for authorized dispense of medicines to an individual at pre-defined and pre-programmed time to ensure proper dosage of medicines, to prevent over dosage of medicines and the omission of prescribed medication, and drug abuse, is illustrated. The system, in accordance with the most preferred embodiment of the present invention includes at least one enclosure with a dispenser unit containing an integrated cap with an interior seal and a plurality of dispensing slots located proximate to the enclosure. The dispensing slot contains at least one medicine and is adapted to facilitate dispense of at least one medicine to an authentic user after validation of authorization.

The driving mechanism for the upward and downward movement of the dispenser unit along the vertical length of the enclosure includes the functioning of a stepper motor with a shaft, a lead pitch screw having the end-points fixed in a pair of screw-guides containing a circlip each, a nut positioned on the lead pitch screw and holding the dispensing unit facilitates the conversion of rotational movement of the lead pitch screw into a linear movement.

Typically, in accordance with the present invention, there is provided a control unit for controlling the functioning of a plurality of functional units of the system, a primary sensor unit functionally coupled to the control unit, a power supply unit functionally coupled to the control unit, a micro-universal serial bus functionally coupled to the control unit, a global navigation satellite system module functionally coupled to the control unit, a set of status indicators having a liquid crystal display, a speaker, and a light emitting diode and functionally coupled to the control unit, a set of knobs functionally coupled to the control unit, and a communication facilitator functionally coupled to the control unit adapted to enable communication between the system and a remote server wherein the remote server enables a medical professional to receive a plurality of inputs including information on the usage pattern of a medicine.

Typically, in accordance with the present invention, the system for authorized dispense of medicines to an individual at pre-defined and pre-programmed time to ensure proper dosage of medicines, to prevent over dosage of medicines and the omission of prescribed medication, and drug abuse, is configured to function in at least one functioning mode selected from the group of stand-alone mode and a paired mode. Further, in each mode of operation, the system is configured to have a plurality of internet of things [IoT] modules.

Additionally, in accordance with the present invention, as an alternative embodiment, the system for authorized dispense of medicines to an individual at pre-defined and pre-programmed time to ensure proper dosage of medicines, to prevent over dosage of medicines and the omission of prescribed medication, and drug abuse is configured to function in stand-alone mode of operation for the dispensing of liquid medicines.

BRIEF DESCRIPTION OF THE ACCOMPANYING DRAWINGS

A more complete understanding of the present invention and advantages thereof may be acquired by referring to the following description and the accompanying drawings in which like reference letters and numerals indicate the corresponding parts in various figures. The accompanying drawings, which are incorporated in and form part of the specification, illustrate exemplary embodiments of the present invention and, together with the description, serve to explain the present invention. Shown are:

It is clearly stated herein that the explanation of the system in the foregoing drawings and the disclosure of the invention in the following description are purely exemplary in nature and any possible alternative or modified system is within the scope and ambit of the present invention.

DETAILED DESCRIPTION

In order to ameliorate one or more drawbacks associated with the prior art and to achieve the aforementioned goals and objects, a portable system for authorized dispensing of medicines to an individual at pre-defined and pre programmed time to ensure proper dosage of medicines, to prevent over dosage of medicines and the omission of prescribed medication drug abuse, is illustrated. Reference will now be made in detail to the preferred embodiments of the present invention, examples of which are illustrated in the accompanying drawings. Embodiments of the present invention are directed to address the aforementioned drawbacks.

While the present invention will be discussed in conjunction with the preferred embodiments, it will be understood that they are not intended to limit the invention to these embodiments. In the following detailed description of the present invention, numerous specific details are set forth in order to provide a thorough understanding of the present invention. However, the invention may be practiced without these specific details. In other instances, methods, procedures, and components have not been described in detail as not to unnecessarily obscure the aspects of the present invention. As used in the specification and the appended claims, the term "medicine" shall mean and include among others, any ingestible medicine, whether it be pill, pill-like items such as tablets, capsules, drugs, vitamins, herbs and the like.

The portable system of the present invention may be used either in stand-alone mode configuration or in paired-mode configuration, wherein the paired-mode configuration requires the pre-pairing of the system with at least one smart device via either a wireless communication mode or a wired communication mode, the smart device being selected from the group consisting of a smartphone, or a laptop, or a tablet, and the like. These wireless and wired modes of paired-mode configuration of the portable system of the present invention are intended at dispensing a medicine to an authorized user, with one kind of the authorization of the user by a medical professional, preferably a pharmacist, at his end, in order to prevent the misuse of the system.

Figure 1:
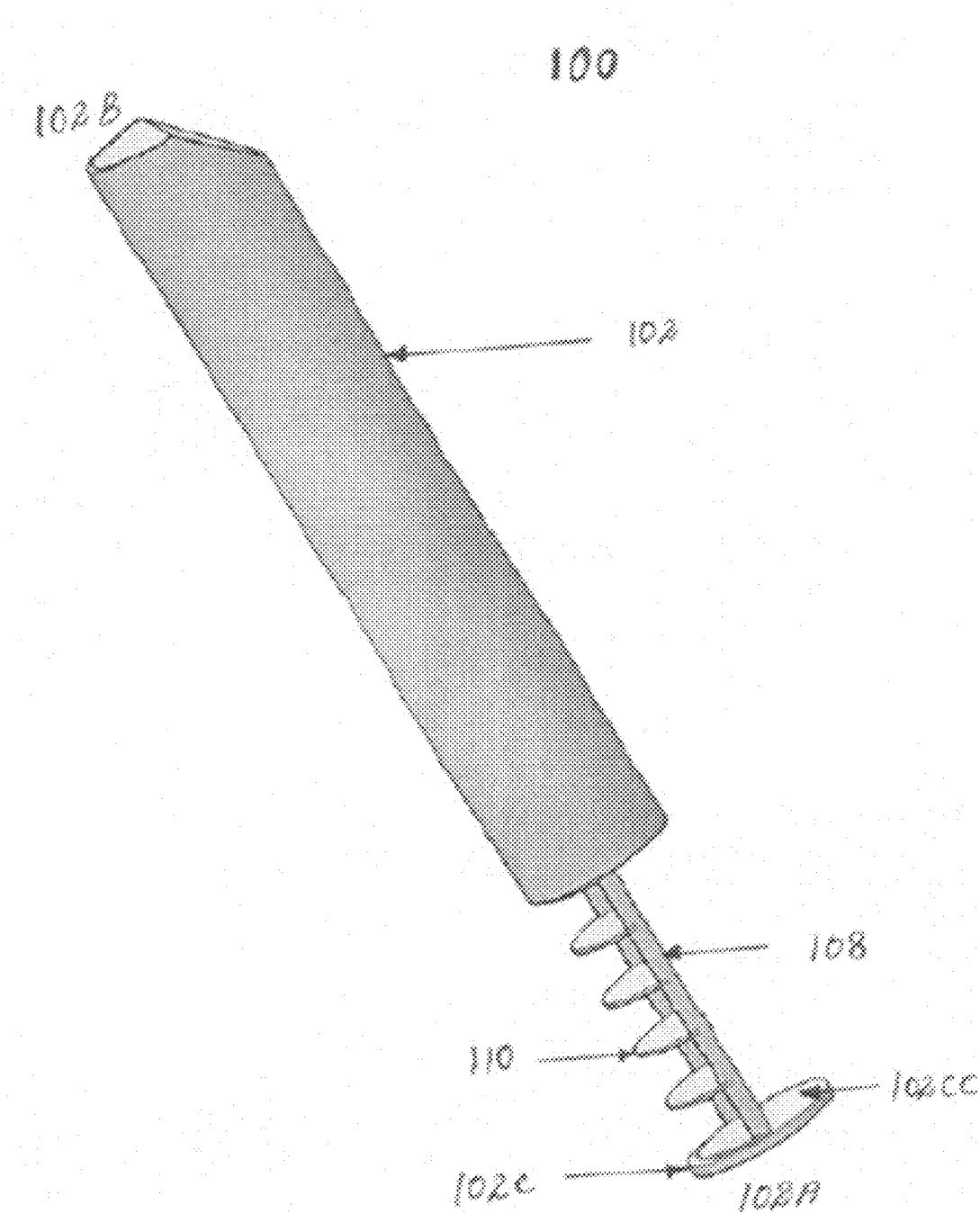
FIG. 1 illustrates a three-dimensional [3D] view of a preferred embodiment of the system in accordance with the present invention.

Referring now to FIG. 1, in accordance with a preferred embodiment of the present invention, there is disclosed a portable system 100 for authorized dispensing of medicines, in stand-alone mode of operation, to an individual at pre-defined and pre-programmed time to ensure proper dosage of medicines, to prevent over dosage of medicines, to prevent the omission of prescribed medications and to prevent drug abuse. The system 100 in accordance with the present invention includes a three dimensional [3-D] enclosure 102. The three-dimensional enclosure 102 is an aesthetically designed, preferably cylindrical shaped, enclosure with its one end 102A capable of both opening and closing and is referred to as top end. The other end 102B is always closed and is referred to as bottom end. There is provided a dispenser unit 108 contained in the three-dimensional enclosure 102. The dispenser unit 108 is configured to structurally comprise, successively continuing along the length, a plurality of dispensing slots 110. Each such dispensing slot 110 is configured to contain at least one printed icon (not shown in the drawings) adapted to indicate the time slot for dispensing a medicine. An integrated cap 102C with an interior seal 102CC, associated with the dispenser unit 108 is provided to facilitate the closing and opening of the top end 102A of the enclosure 102. The enclosure 102, the dispenser unit 108 and the plurality of dispensing slots 110 are made of a composite polymer characterized by resistance to chemicals, thermal resistance and impact resistance. Further, the composite polymer used for the structural design of the enclosure 102, the dispenser unit 108 and the plurality of dispensing slots 110 has strength, stiffness, high strength-to-weight ratio and exceptional dimensional stability. Generally, thermoplastic materials like acrylonitrile butadiene styrene (ABS) and Carbon-fiber-reinforced thermoplastic (CFRP or CRP or CFRTP) are preferably used in the construction of the enclosure 102, the dispenser unit 108 and the plurality of dispensing slots 110.

Figure 2:
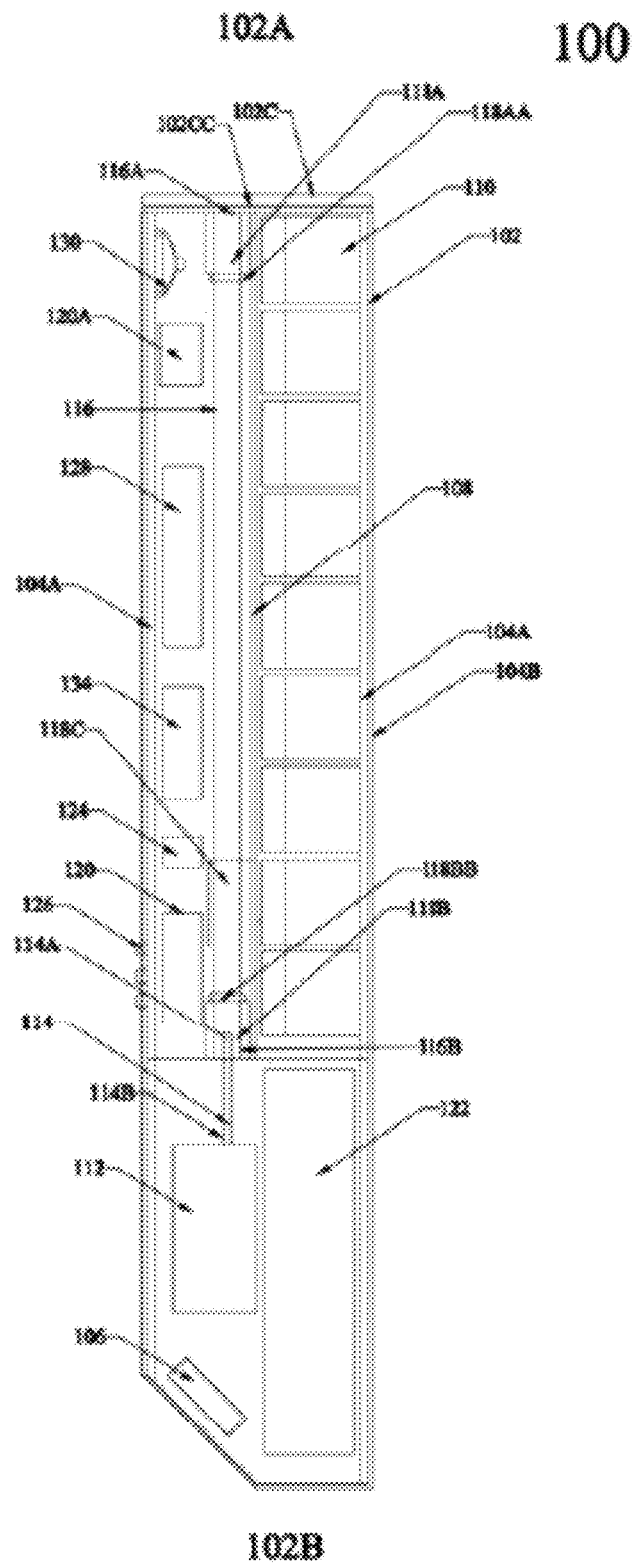
FIG. 2 illustrates a sectional view of the preferred embodiment of the system shown in FIG. 1 in accordance with the present invention.

Referring now to FIG. 2, various structural and functional elements of the system 100, in accordance with the preferred embodiment of the present invention are illustrated. The enclosure 102 is a tamper-proof, thin double walled, with the detachably split internal wall 104A and an outer rigid wall 104B. The enclosure 102 is adapted to hold the dispenser unit 108. The dispenser unit 108 is configured in such a way as to pass through a pair of guide-ways [not shown in the drawings]. Each such dispensing slot 110 is adapted to comprise either a single medicine or a variety of medicines. The size and shape of each such dispensing slot 110 is unique, regular and intended at fulfilling the purpose of the invention by making the dispensing of the medicines from a given slot 110. The finite number of dispensing slots 110 used in the dispenser unit 108 is selected in such a way as to enable a pharmacist to refill the empty dispenser slots 110 at regular time period intervals with the help of a semi-automated pill dispenser (not shown in the drawings). The dispenser unit 108 is enabled to linearly move inside and along the length of the enclosure 102 via the end 102A.

There is provided a stepper motor 112 to facilitate the movement of the dispenser unit 108 along the length of the enclosure 102. The motor 112 is preferably a geared stepper motor, having a metallic shaft 114 thereon, providing the sufficient torque for the movement of the dispenser unit 108. One end 114A of the metallic shaft 114 is functionally and structurally coupled to a long, thin, fine lead pitch screw 116 by way of insertion. The lead pitch screw 116 is off-centered and positioned near and adjacent to the side of the detachable split internal wall 104A of the enclosure 102. The lead pitch screw 116 is configured to run along the length of the three-dimensional enclosure 102. The lead pitch screw 116 runs parallel to the cylindrical axis of the enclosure 102.

A pair of screw-guides 118A and 118B is adapted to receive the lead pitch screw 116. In accordance with an aspect of the present invention, the screw-guide 118A is positioned near the integrated cap 102C. One end 116A of the lead pitch screw 116 passing through the screw-guide 118A and positioned near the cap 102C is referred to as the top-end. The other end 116B of the lead pitch screw 116 passing through the screw-guide 118B is referred to as the bottom-end. The set of screw-guides 118A and 118B are configured to hold the lead pitch screw 116 such that the rotary motion of the lead pitch screw 116 is enabled and the linear backward and forward motion of the screw 116 is discontinued. These screw-guides 118A and 118B are made of alloys, preferably brass, to reduce the friction and wear and tear. There is provided a nut 118C on and along the length of the lead pitch screw 116, on which the dispenser unit 108 is glued. The nut 118C is adapted to facilitate the conversion of the rotational movement of the screw 116 into linear movement, thereby enabling upward and downward movement of the dispenser unit 108 on the lead pitch screw 116. Further, there is a pair of circlips 118AA and 118BB provided respectively near the screw-guides 118A and 118B to facilitate the prevention of the upward and the downward movement of the lead pitch screw 116.

A control unit 120 is provided in the system 100, within the enclosure 102. The control unit 120 is adapted to facilitate the control and maintenance of smooth functioning of a plurality of functional units within system 100. The plurality of functions includes, among others, rising and lowering of the dispenser unit 108 on the lead pitch screw 116, functioning of the stepper motor 112 and the like.

In an additional aspect of the preferred embodiment of the present invention, there is provided a power supply unit 122 functionally coupled to the control unit 120 and adapted to provide power supply for a plurality of operations including the functioning of the stepper motor 112, rising and lowering of the dispenser unit 108 on the lead pitch screw 116 and the like. The power supply unit 122 is preferably a rechargeable battery. However, a super capacitor may also be used as an alternative source for the power supply. The rechargeable battery in the power supply unit 122 is preferably a lithium-ion [Li-ion] battery.

A micro universal serial bus [USB] connector 124 is provided in the system 100. The micro universal serial bus 124 is functionally coupled to the control unit 120 and is adapted to recharge the rechargeable battery in the power supply unit 122.

A primary sensor unit 106 is provided in the system 100. In accordance with the aforementioned preferred embodiment of the present invention, the primary sensor unit 106 is embedded in, at and near the closed end 102B of the enclosure 102. The primary sensor unit 106, in the stand-alone mode configuration of the system 100 is basically a semiconductor based biometric sensor. The primary sensor unit 106 is adapted to facilitate the identification and authorization of a user of the system 100 and also to provide the user with access control. The primary sensor unit 106 is adapted to preferably utilize at least one finger print characteristics for the identification and authorization of the user of the system 100. When the system 100 is operated in stand-alone mode, the finger print characteristic is the only biometric characteristic for the identification and authorization of the user.

In a further aspect of the preferred embodiment of the present invention, there is provided a set of knobs 126 functionally coupled to the control unit 120. The set of knobs 126 is adapted to perform a plurality of tasks including but not limited to controlling the operation of the system 100, refilling the system 100 by filing the dispenser unit 108, reset the operation of the system 100 and the like.

There is provided a global navigation satellite system [GNSS] module 120A functionally coupled to the control unit 120. The global navigation satellite system module 120A is adapted to facilitate a user of the system 100 to track down the exact geographical location wherein the system 100 is being located.

At least one liquid crystal display [LCD] unit 128, at least one speaker 130, at least one light emitting diode (not shown in the drawings), and at least one vibrator (not shown in the drawings) included inside the system 100, are provided wherein each such liquid crystal display, speaker, vibrator (not shown in the drawings), and the light emitting diode (not shown in the drawings), distinctly coupled with the control unit 120 are adapted to function as status indicators. The status indication generated by the aforementioned liquid crystal display unit 128, or the speaker 130 or the light emitting diode (not shown in the drawings) include the display of at least one status indication selected from the group consisting of a plurality of indications including when the next medicine is due, un-authorization of the user due to mismatching biometric characteristic and the like. Further configuration of the system 100 includes the status indication to be either in the form of display on the screen of the liquid crystal display unit 128, or the generation of beep from the speaker 130, or the light emitted from the light emitting diode (not shown in the drawings) or the vibration generated by the vibrator (not shown in the drawings), in order to indicate the current status of the system 100. The generation of beep varies with the status indication. The set of knobs 126, the liquid crystal display unit 128, speaker 130 and light emitting diode (not shown in the drawings) are adapted and engineered in such a way to prevent the passage of air into the system 100 in order to protect the solid medicines from the effect of moisture, preferably by the way of sealing, except during the time of medicine dispense and at the time of refilling the dispenser unit 108. The refilling includes the refilling of pre-determined set of medicines for the pre-determined time slots of the pre-determined date. Further, in an additional aspect of the preferred embodiment of the present invention, the liquid crystal display unit 128 is configured to display the balance quantity of medicine available in the system 100 and further configured to display the due date of refilling the medicines into the system 100 wherein the refilling includes the refilling of pre-determined set of medicines for the pre-determined time slots of the pre-determined date.

A communication facilitator 134 is provided in the system 100. The communication facilitator 134 is functionally coupled to the control unit 120. The communication facilitator 134 is preferably a two-way wireless communication device like modem connected to a remote server. The frequency and power level of radiation are chosen to be generic to medical devices to have least interference possible. The communication facilitator 134 enables the two-way communication between the system 100 and a remote server (not shown in the drawings) containing a plurality of medical records. The remote server (not shown in the drawings) enables a medical professional including but not limited to a physician and a pharmacist to receive a plurality of inputs including information on the usage pattern of medicine. The communication facilitator 134 is configured to function preferably in a low power local area network [LAN] to enable reduced frequency of recharging of the system 100. However, the communication facilitator 134 may also be configured to function in a high power wide area network [WAN]. Further, the two-way wireless communication device 134 is adapted to facilitate a medical professional including a physician and a pharmacist with the usage data to confirm authorized usage. The usage data is further used for exploratory analysis and statistical analysis and data extended analysis.

After receiving the requirement of the user through the primary sensor unit 106, the control unit 120 ensures the availability of the tablet or the pill through a set of internal computations with respect to the pre-programmed data at the time of refilling and the number of times of dispensing of the tablets or pills. The control unit 120 transmits the functioning signal to the stepper motor 112. The stepper motor 112, after receiving the functioning signal from the control unit 120 is adapted to facilitate the upward movement of the dispenser unit 108 to enable the ejection of at least one tablet or a pill from at least one dispensing slot 110.

When a medicine is dispensed or ejected out depending on the request and the requirement of the user of the system 100, via the primary sensor unit 106, the record in the database pertaining to a particular user of the system 100, maintained in the remote server (not shown in the drawings), is consequently and automatically updated. In cases, where there is no pill in the slot or the dispensed pill has fallen down, the user is facilitated to request for a re-authorization for the dispensing of the medicine. Such request for reauthorization is authorized either by a medical professional including but not limited to a physician or a pharmacist assisted by the database or by built-in algorithms validating the authenticity of such request for reauthorization. The reauthorization for the dispense of a medicine either by the medical professional or by the built-in algorithms as explained above, changes the time slot of dispense of a medicine and therefore the plurality of printed icons contained in the dispensing slots 110 enable the user to choose the appropriate medicine. The automatic updating of the record in the database pertaining to the user is communicated to the medical professional including a pharmacist and a physician via the communication facilitator 134 associated with the system 100. When the stock of the tablets or pills in the system 100 is nearing emptiness, during the regular functioning of the system 100, the plurality of dispensing slots 110 in the dispensing unit 108 of the system 100 are to be refilled by the pharmacist wherein the refilling includes the refilling of pre-determined set of medicines for the pre-determined time slots of the pre-determined date, with the help of a semi-automated pill dispenser (not shown in the drawings). The pharmacist is required to refill the dispensing slots 110, using his or her authorization. The medicine to be refilled includes pills, pill-like items such as tablets, capsules, drugs, vitamins, herbs and the like. The database of the user using the system 100 is once again updated at the time of complete refilling of the system 100. The information of the complete refilling of the dispenser unit 108 of the system 100 and the updating of the database of the user is communicated by the pharmacist via the communication facilitator 134 to the user of the system 100 via the control unit 120.

Figure 3A:
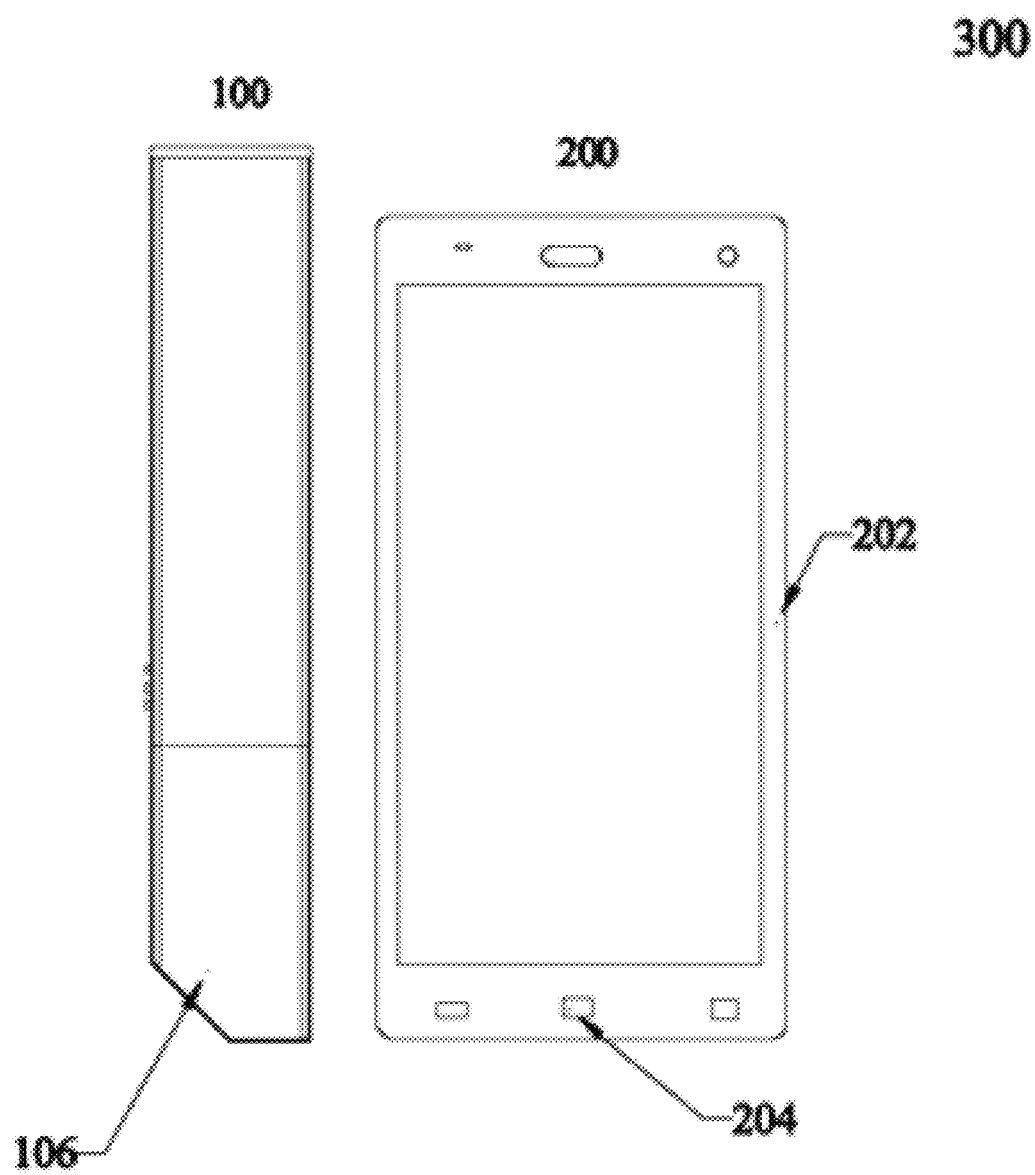
FIG. 3A illustrates a schematic of an additional embodiment of the system in accordance with the present invention.
Figure 3B:
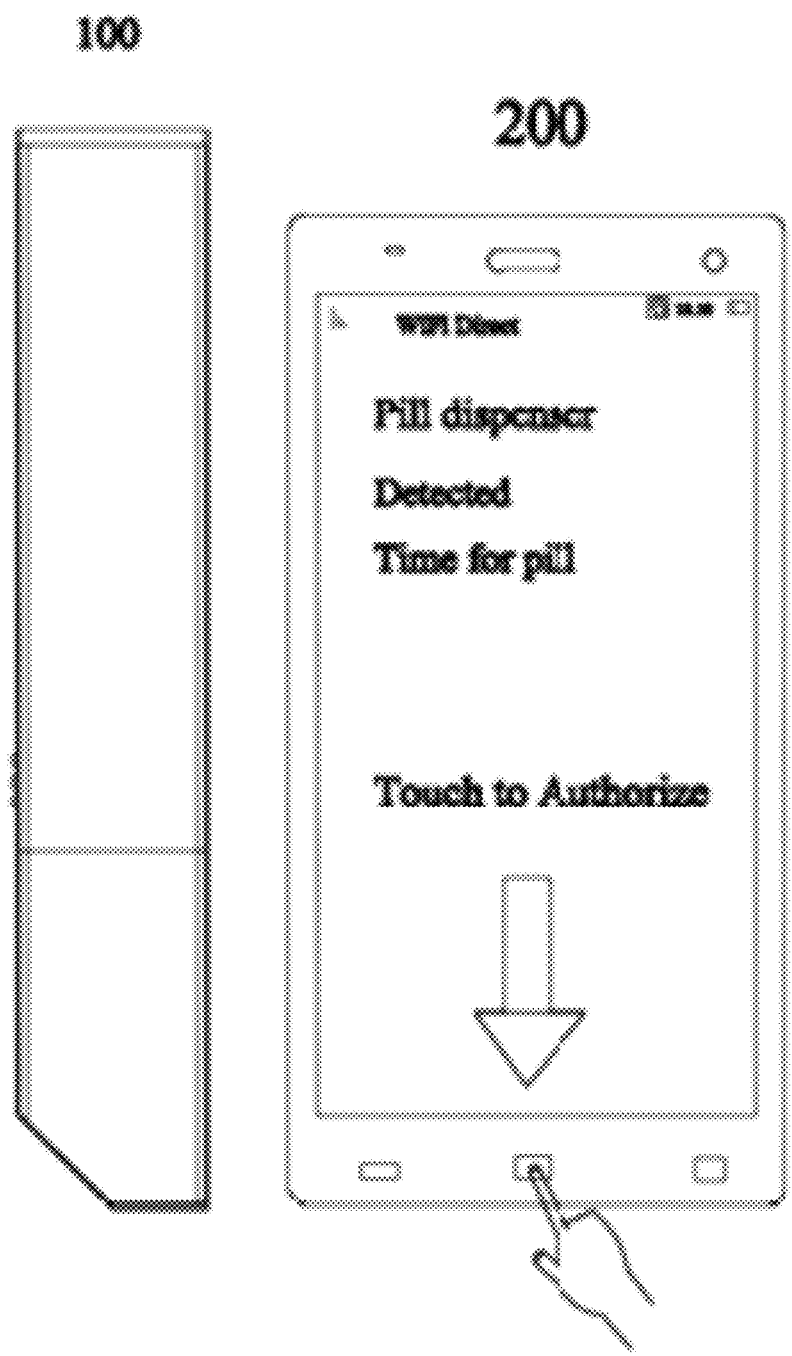
FIG. 3B illustrates a schematic of the additional embodiment of the system in accordance with the present invention.

Referring now to FIG. 3A and FIG. 3B, in accordance with an additional embodiment of the present invention, there is disclosed and illustrated, a portable system 300 for authorized dispensing of medicines, in paired wireless configuration, to an individual at pre-defined and preprogrammed time to ensure proper dosage of medicines, to prevent over dosage of medicines, to prevent the omission of prescribed medications and to prevent drug abuse. The system 300, in accordance with the present invention, comprises two main functional systems 100 and 200 paired in wireless configuration, wherein the system 200 is a pairing smart device.

The system 100 in accordance with this additional embodiment of the present invention and integral part of the system 300 is identical to the system 100 disclosed in the aforementioned discussion pertaining to the description of the various functional elements in the most preferred embodiment of the present invention in stand-alone configuration, in reference to the drawings viz., FIG. 1 and FIG. 2 respectively. Therefore, the pairing system 200 and the relevant functioning in wireless pairing with system 100 is illustrated.

The pairing system 200 in accordance with the additional embodiment of the present invention illustrating paired wireless configuration comprises a smart functional unit 202 for pairing with the system 100. The smart functional unit 202 is a smart device that can be coupled to the system 100 via a plurality of wireless protocols. The smart device utilized in pairing includes at least one electronic device selected from the group consisting of a smartphone, or a laptop, or a tablet, and the like. The smart functional unit 202, on its surface, contains a secondary sensor unit 204. The primary sensor unit 106 of the system in conjunction with the secondary sensor unit 204 associated with the pairing smart device 202 in the system 300 is enabled to receive the user specific characteristics for authorization. The system 100 is usually in low power Wi-Fi mode. However, at pre-determined time slots for the dispensing of the medicines, the system 100 connects with the pairing smart device 202 of the system 300 in wireless mode of communication including but not limited to Wi-Fi Direct mode of communication.

At the initial stage of operation, the system 300 and in particular, the smart device 202 is configured to generate an alerting sound signal in accordance with the pre-programmed time for the medication. Consequently, there is a display on the screen of the smart device 202 requesting the authorization of the user. The user is required to provide the input to the authorization request by giving his or her unique user characteristic on the designated secondary sensor unit 204 provided on the surface of the smart device 202. Once the authorization of the user is validated, the functioning of the system 100 to dispense the medicine as required and the requested by the authorized user is initiated.

Figure 4A:
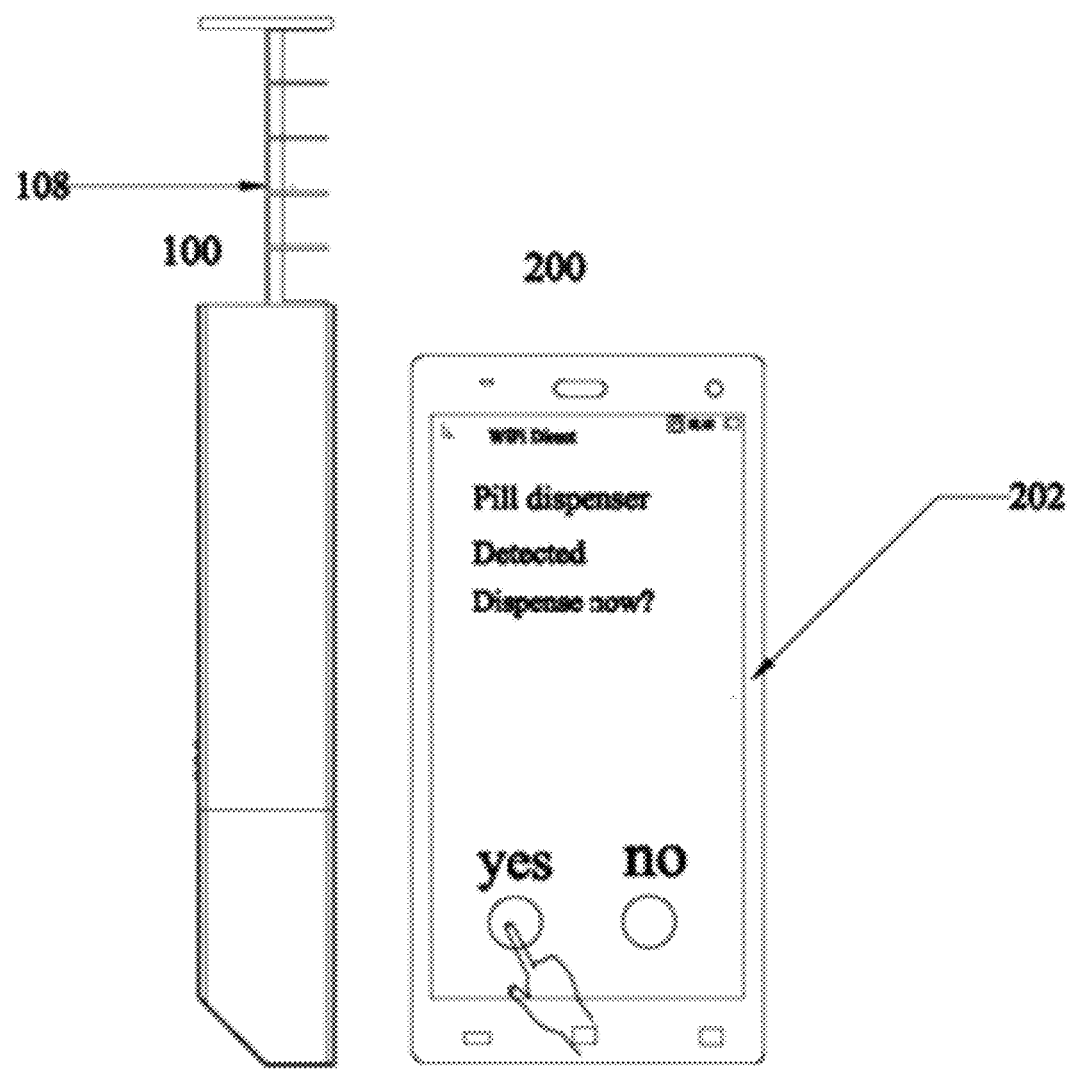
FIG. 4A illustrates a schematic of the additional embodiment of the system in accordance with the present invention.

Referring now to FIG. 4A, the functioning of the system 200, in accordance with this additional embodiment of the present invention is illustrated. In the first step, the system 200 initiates the display of the message like 'Dispense now?' on the screen of the smart device 202 with two options for the user as 'YES' and 'NO'. If the user selects the option 'NO', there will not be any initiation of the functioning of the system 100 that has been paired with the smart device 202. Therefore, there is no dispense or the ejection of medicine by the system 100. However, if the user selects the option 'YES', there is the initiation of the functioning of the system 100 that has been paired with the smart device 202. There is the dispensing of the medicine by the system 100 as required and requested by the user. In both the cases, the functioning of the system 100 is as disclosed, illustrated and explained in the previous sections of the detailed description in this specification in accordance with FIG. 1 and FIG. 2.

Figure 4B:
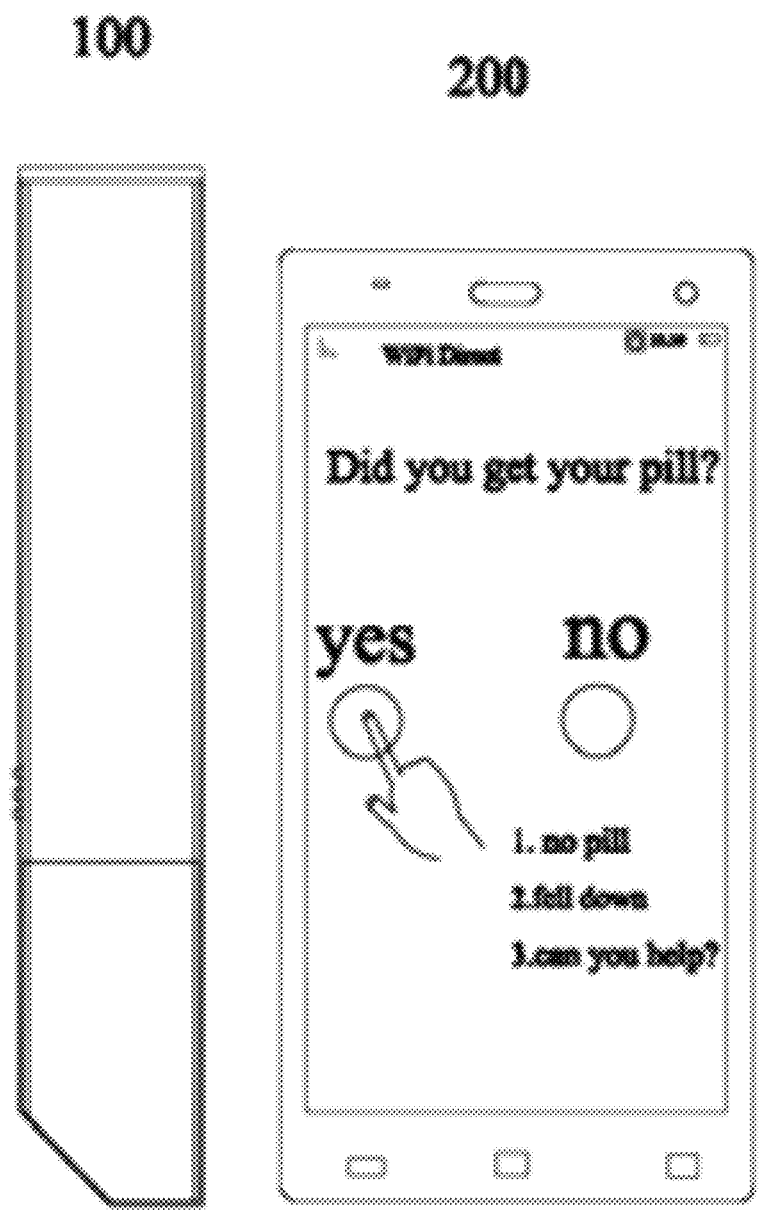
FIG. 4B illustrates a schematic of the additional embodiment of the system in accordance with the present invention.

Referring now to FIG. 4B, at the very instant of dispense or ejection of the medicine by the system 100, there is an initiation of the display of a second message like 'Did you get the pill?' on the screen of the smart device 202 with two options for the user 'YES' or NO'. If the user chooses the option 'YES', then the dispensing unit 108 retracts back the same distance that matches with the distance covered during dispensing of the medicine. The record of the particular user is updated in the remote server. Further, the update of the record is communicated to the corresponding medical professional including a physician and a pharmacist. If, on the other hand, the user chooses the option 'NO', there will be display of a plurality of secondary options like 'no pill', 'pill fell down', and 'can you help' and the like. In accordance with the choice of any one option selected from these secondary options displayed on the screen of the smart device 202, the medical professional including the pharmacist and the physician, at the other end, receives the information from the remote server and takes a decision as to initiate the immediate dispensing of another pill for the user based on the analyzed information from the database. Alternatively, the built-in algorithms along with the database analyses the request and ascertains the authenticity of the request by the user and initiates the reauthorization enabling the end user to receive another set of medicine through the system 100. The database record of the user in the remote server is updated accordingly. The reauthorization for the dispense of a medicine either by the medical professional or by the built-in algorithms as explained above, changes the time slot of dispense of a medicine and therefore the plurality of printed icons contained in the dispensing slots 110 enable the user to choose the appropriate medicine.

Figure 5A:
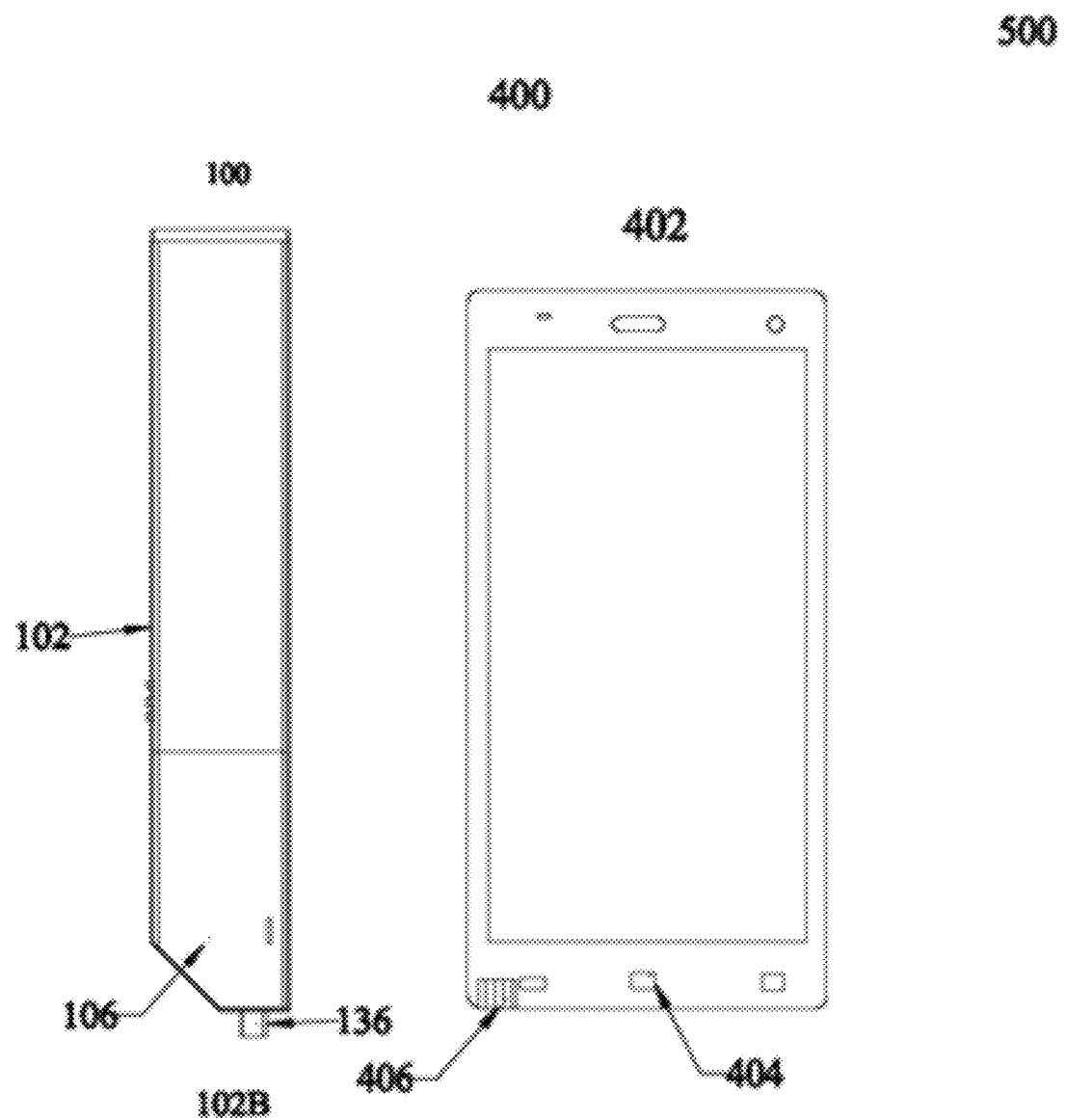
FIG. 5A illustrates a schematic of a further embodiment of the system in accordance with the present invention.
Figure 5B:
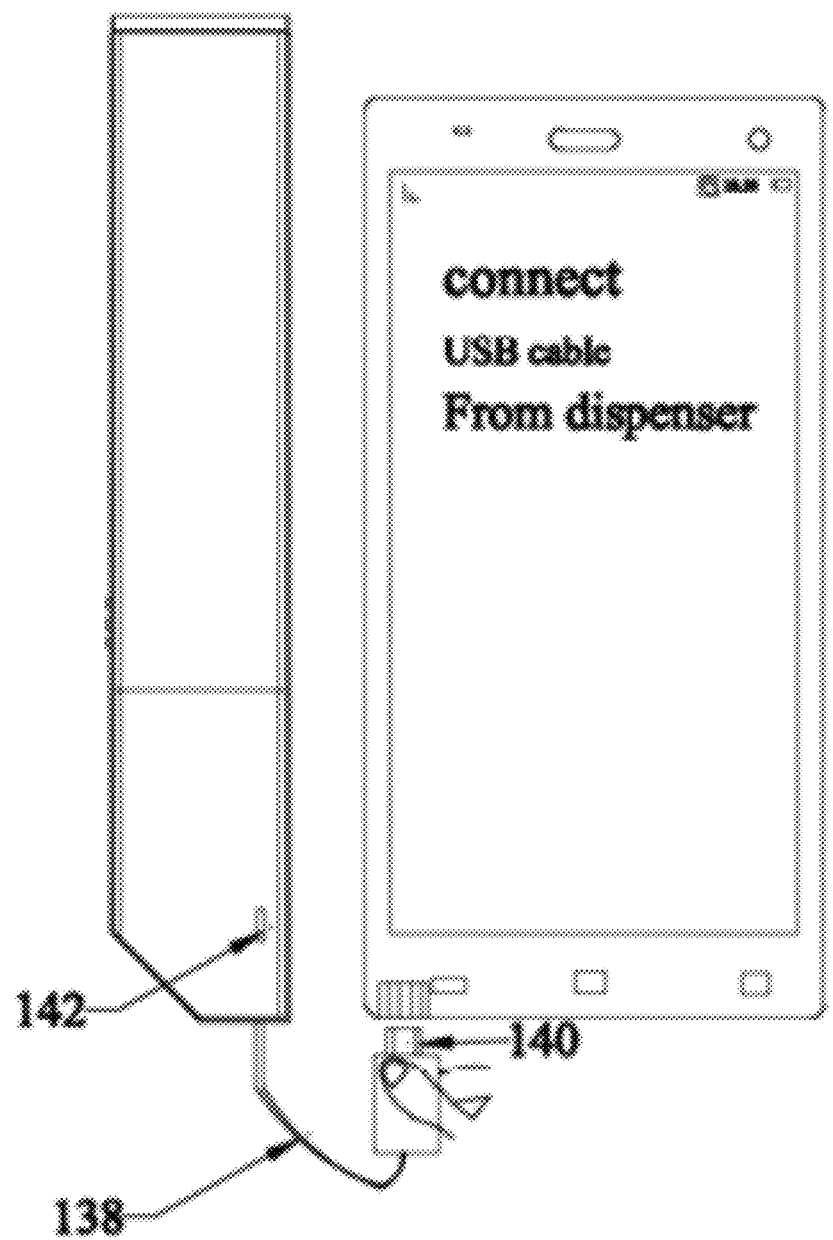
FIG. 5B illustrates a schematic of the further embodiment of the system in accordance with the present invention.

Referring now to FIG. 5A and FIG. 5B, in accordance with a further embodiment of the present invention, there is disclosed and illustrated, a portable system 500 for authorized dispensing of medicines, in paired wired configuration, to an individual at pre-defined and preprogrammed time to ensure proper dosage of medicines, to prevent over dosage of medicines, to prevent the omission of prescribed medications and to prevent drug abuse. The system 500, in accordance with the present invention, comprises two main functional systems 100 and 400 paired in wired configuration, wherein the system 400 is a pairing smart device.

The system 100 in accordance with this additional embodiment of the present invention and integral part of the system 500 is identical to the system 100 disclosed in the aforementioned discussion pertaining to the description of the various functional elements in the most preferred embodiment of the present invention, in reference to the drawings viz., FIG. 1 and FIG. 2 respectively. Therefore, the pairing system 400 and the relevant functioning in wired pairing with system 100 is illustrated.

The pairing system 400 in accordance with the additional embodiment of the present invention illustrating paired wired configuration comprises a smart functional unit 402 for pairing with the system 100. The smart functional unit 402 is a smart device that can be coupled to the system 100 via a communication wire. The smart functional unit 402, on its surface, contains a secondary sensor unit 404. The primary sensor unit 106 of the system in conjunction with the secondary sensor unit 404 associated with the pairing smart device 402 in the system 500 is enabled to receive the user specific characteristics for authorization. There is provided a device communication point 406 near the secondary sensor unit 404 on the surface of the smart device 402, facilitating the wired communication with the system 100. The smart device 402 utilized in pairing includes at least one electronic device selected from the group consisting of a smartphone, or a laptop, or a tablet, and the like. Both the system 100 and the smart device 402 are in low power mode. Therefore, the display screen of the smart device 402 is preferably shown blank.

In addition, preferably near the bottom end 102B of the enclosure 102 of the system 100, there is provided a system communication point 136 having a communication wire 138 with a communication socket 140 thereon, enabling the wired communication with external pairing devices such as the smart device like the device 402. The communication wire 138 with the communication socket 140 may be extended by rolling a tiny wheel like structure 142 provided on the outer surface of the of the enclosure 102 of the system 100. Further, for the system 100, to be paired with the smart functional unit 402 in the paired wired configuration, a super capacitor is used as an alternative to the rechargeable battery in the power supply unit 122. The super capacitor in the power supply unit 122 provides the power supply for a plurality of functional units excluding the stepper motor 112. In this paired wired configuration, the stepper motor is driven by the power supply for the external smart functional unit 402.

At the initial stage of operation, the system 500 and in particular, the smart device 402 is configured to configured to generate an alerting sound signal in accordance with the pre-programmed time for the medication. Consequently, there is an appearance of message like 'Connect USB cable' on the screen of the smart device 402. The message is displayed to request the concerned user to connect the smart device 402 to the system 100 via the wired communication mode by connecting the communication wire 138 to the smart device 402.

Figure 6A:
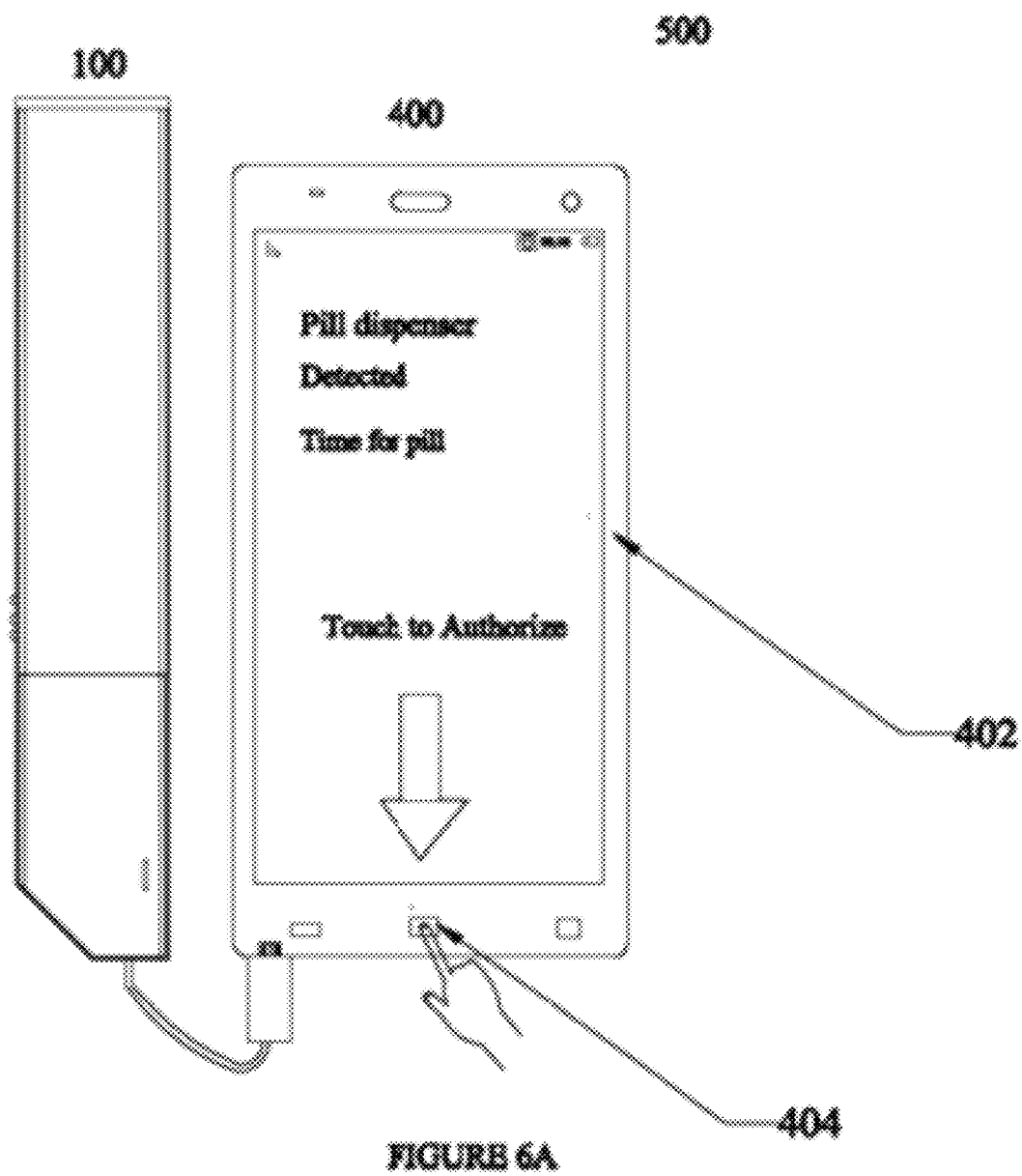
FIG. 6A illustrates a schematic of the further embodiment of the system in accordance with the present invention.

Referring now to FIG. 6A, at the initial stage of operation, the system 500 and in particular, the smart device 402 is configured to request the authorization of the user. The user is required to input user specific unique characteristic to the secondary sensor unit 404 provided on the surface of the smart device 402. Once the authorization of the user is validated, the functioning of the system 400 to dispense the medicine as required and the requested by the authorized user is initiated.

Figure 6B:
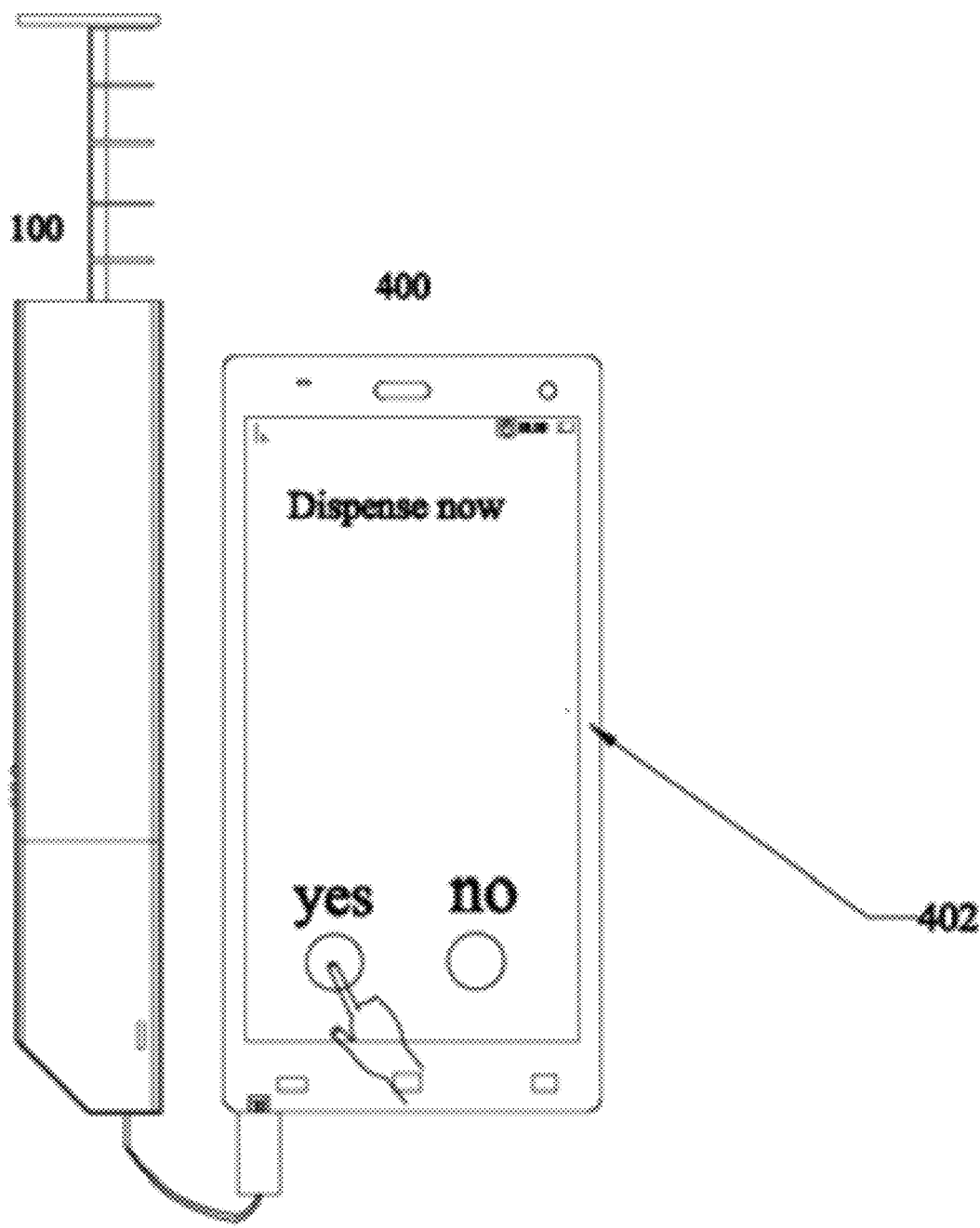
FIG. 6B illustrates a schematic of the further embodiment of the system in accordance with the present invention.

Referring now to FIG. 6B, the functioning of the system 400, in accordance with this additional embodiment of the present invention is illustrated. In the first step, the system 400 initiates the display of the message like 'Dispense now?' on the screen of the smart device 402 with two options for the user as 'YES' or 'NO'. If the user selects the option 'NO', there will not be any initiation of the functioning of the system 100 that has been paired with the smart device 402 via the wired connection. Therefore, there is no dispense or the ejection of medicine by the system 100. However, if the user selects the option 'YES', there is the initiation of the functioning of the system 100 that has been paired with the smart device 402. There is the dispensing of the medicine by the system 100 as required and requested by the user. In both the cases, the functioning of the system 100 is as disclosed, illustrated and explained in the previous sections of the detailed description in this specification in accordance with FIG. 1 and FIG. 2.

Figure 7:
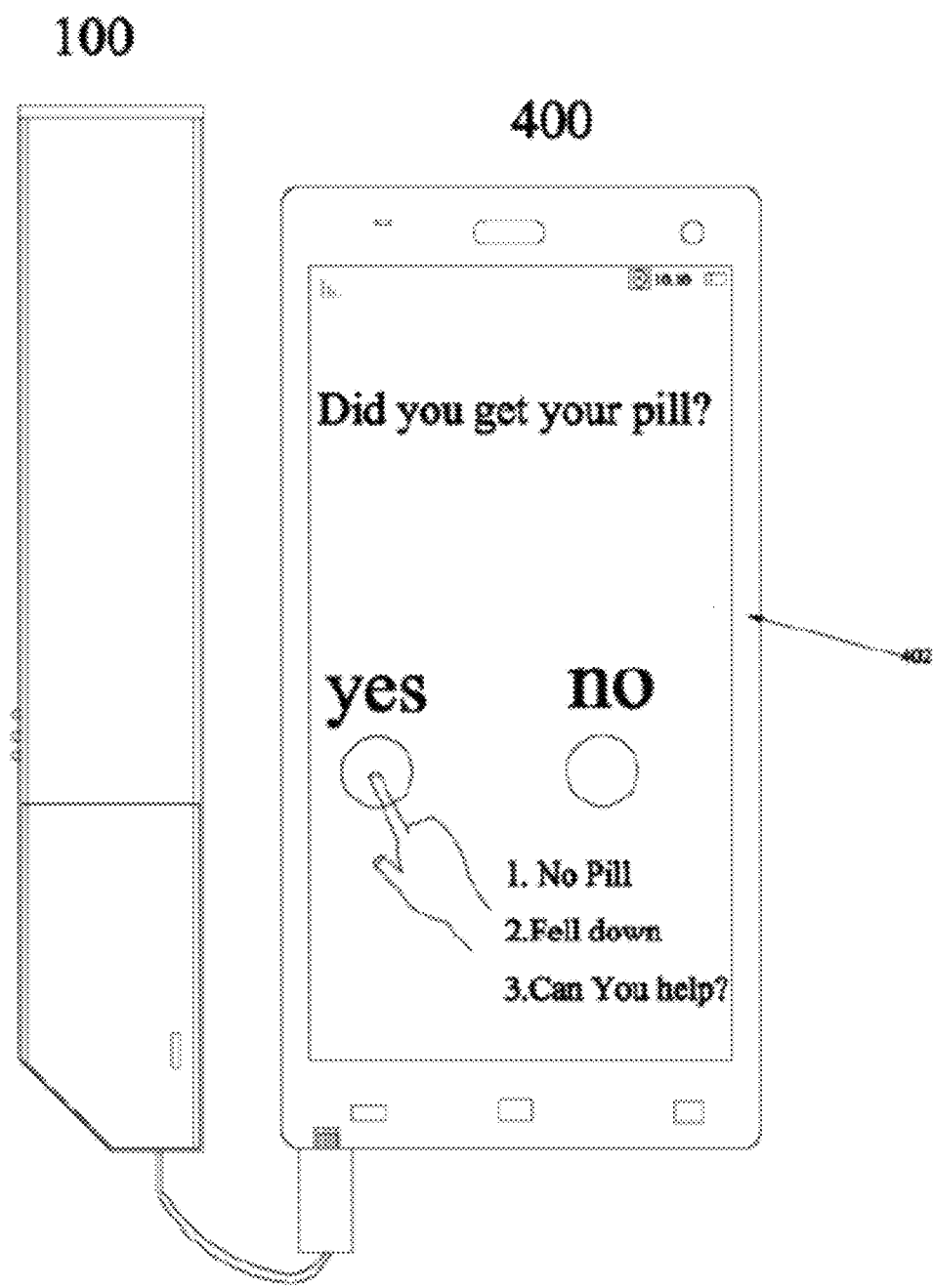
FIG. 7 illustrates a schematic of the further embodiment of the system in accordance with the present invention.

Referring now to FIG. 7, at the very instant of dispense or ejection of the medicine by the system 100, there is an initiation of the display of a second message like 'Did you get the pill?' on the screen of the smart device 402 with two options for the user 'YES' or 'NO'. If the user chooses the option 'YES', then the dispensing unit 108 retracts back the same distance that matches with the distance covered during dispensing of the medicine. The record of the particular user is updated in the remote server. Further, the update of the record is communicated to the corresponding medical professional including a physician and a pharmacist. If, on the other hand, the user chooses the option 'NO', there will be display of a plurality of secondary options like 'no pill', 'pill fell down', and 'can you help' and the like. In accordance with the choice of any one option selected from these secondary options displayed on the screen of the smart device 402, the medical professional including the pharmacist and the physician, at the other end, receives the information received from the server and takes a decision as to initiate the immediate dispensing of another pill for the user based on the analyzed information from the database. Alternatively, the built-in algorithms along with the database analyses the request and ascertains the authenticity of the request by the user and initiates the reauthorization enabling the end user to receive another set of medicine through the system 100. The database record of the user in the remote server is updated accordingly. The reauthorization for the dispense of a medicine either by the medical professional or by the built-in algorithms as explained above, changes the time slot of dispense of a medicine and therefore the plurality of printed icons contained in the dispensing slots 110 enable the user to choose the appropriate medicine.

Figure 8:
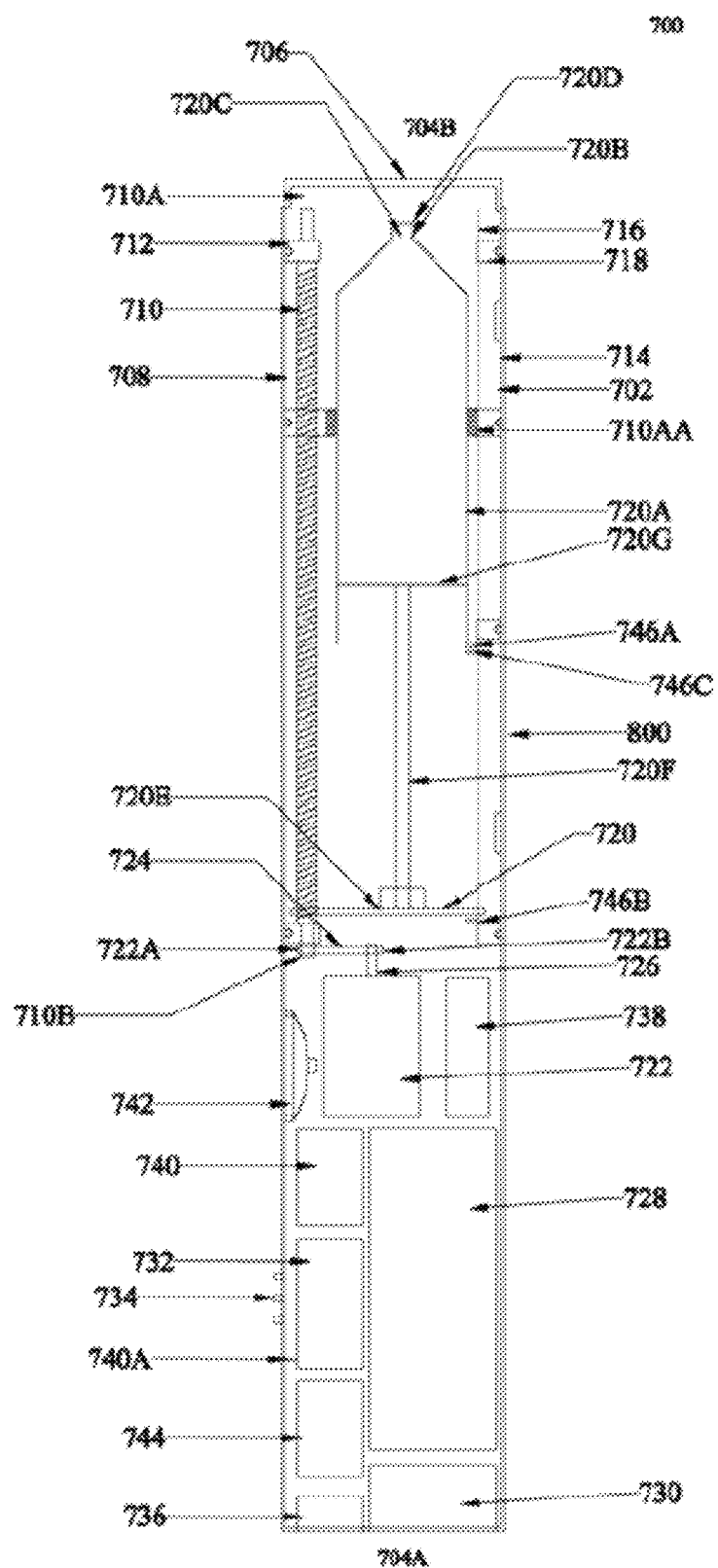
FIG. 8 illustrates a schematic of yet another embodiment of the system in accordance with the present invention.

Referring now to FIG. 8, there is disclosed a medicine dispensing system 700 in accordance with yet another embodiment of the present invention. The system 700 in accordance with the present invention is designed to dispense liquid medicine. The system 700 is configured to function in the stand-alone configuration. The system 700 includes a three dimensional [3-D] enclosure 702. One end 704A of the enclosure 702 is closed and is referred to as the bottom end. The other end 704B of the enclosure 702 is capable of both opening and closing and is referred to as the top end. In accordance with the present invention, near the top end 704B, there is provided a removable cap 706. A disposable liquid medicine dispensing unit 720A in the form of a syringe adapted to carry and dispense a liquid medicine is provided within the enclosure 702. The disposable liquid medicine dispensing unit 720A comprises a small nozzle 720B with an orifice thereon at the tip 720C, a nozzle cap 720D adapted to cover the tip 720C, a bottom end 720E, a piston with a piston-tail 720F near the bottom end 720E and a piston-head 720G. A primary sensor unit 730 is provided in the system 700. In accordance with this yet another embodiment of the present invention, the primary sensor unit 730 is embedded in, at and near the closed end 704A of the enclosure 702. The primary sensor unit 730, in the stand-alone mode configuration of the system 700 is basically a semiconductor based biometric sensor. The primary sensor unit 730 is adapted to facilitate the identification and authorization of a user of the system 700 and also to provide the user with access control. The primary sensor unit 730 is adapted to preferably utilize at least one finger print characteristics for the identification, authentication and authorization of the user of the system 700. When the system 700 is operated in stand-alone mode, the finger print characteristic is the only biometric characteristic for the identification, and authorization of the user.

Within the enclosure 702, below the removable cap 706, at one sidewall 708 of the enclosure 702, there is provided a long, thin screw 710. The screw 710 is a fine lead pitch screw. The lead pitch screw 710 is positioned near to the sidewall 708. Preferably, the lead pitch screw 710 is positioned adjacent to the sidewall 708 of the enclosure 702 in such a way that the length of the lead pitch screw 710 is perfectly parallel to the length of the sidewall 708. The screw 710 is received through a set of screw-guides 712. On the opposite end, near the sidewall 714 of the enclosure 702, there is provided a long, thin pin 716. The long pin 716 is received through a set of pin-guides 718. The long pin 716 is positioned in such a way that the length of the pin 716 is parallel to the length of the sidewall 714. The set of screw-guides 712 is mounted rigidly on the interior of the sidewall 708. The set of pin-guides 718 is rigidly mounted on the interior of the sidewall 714. At least one screw-guide 712 is positioned near the removable cap 706. The end 710A of the screw 710 passing through the screw-guide 712 positioned near the removable cap 706 is referred to as the top end. The other end 710B of the lead pitch screw 710 is referred to as the bottom-end.

A motor, preferably a stepper motor 722 is provided near the bottom-end 710B of the lead pitch screw 710. The stepper motor 722 is functionally coupled to the lead pitch screw 710 via a pair of pulleys 722A and second pulley 722B and a conveyor belt 724. The first pulley 722A is functionally coupled to the bottom-end 710B of the lead pitch screw 710 whereas the second pulley 722B is coupled to the shaft 726 of the stepper motor 722. The conveyor belt 724 is configured to run over the pulleys 722A and 722B. The stepper motor 722 is adapted to facilitate the upward of the downward movement of the disposable liquid medicine dispensing unit 720A on the lead pitch screw 710.

A control unit 732 is provided in the system 700, within the enclosure 702. The control unit 732 is adapted to facilitate control and maintenance of smooth functioning of a plurality of functional units within system 700. The plurality of functions includes but not limited to rising and lowering of the disposable liquid medicine dispensing unit 720A on the lead pitch screw 710, functioning of the stepper motor 722, receiving the inputs from the user in the form of user specific characteristic through the primary sensor unit 730 and the like.

There is provided a power supply unit 728 functionally coupled to the control unit 732 and adapted to provide power supply for a plurality of operations including the functioning of the stepper motor 722, rising and lowering of disposable liquid medicine dispensing unit 720A on the lead pitch screw 710 and the like. The power supply unit 728 is preferably rechargeable battery. The rechargeable battery in the power supply unit 728 is preferably a lithium-ion [Li-ion] battery.

A micro universal serial bus [USB] connector 736 is provided within the system 100. The micro universal serial bus 736 is functionally coupled to the control unit 732 and is further adapted to recharge the rechargeable battery in the power supply unit 728.

In an additional aspect of the present invention, there is provided a set of knobs 734 functionally coupled to the control unit 732. The set of knobs 734 is adapted to perform various functions including but not limited to controlling the operation of the system 700, refilling the system 700, reset the operation and the like.

A global navigation satellite system [GNSS] module 738 is provided and is coupled to the control unit 732. The global navigation satellite system module 738 is adapted to facilitate a user to track down the exact geographical location wherein the system 700 is being located.

At least one liquid crystal display [LCD] unit 740, at least one speaker 742, at least one light emitting diode 740A, and at least one vibrator [not shown in the drawings] are provided wherein each such liquid crystal display 740, speaker 742, the light emitting diode 742A, and the vibrator [not shown in the drawings] distinctly coupled with the control unit 732 are adapted to function as status indicators. The status indication generated by the aforementioned liquid crystal display unit 740, or the speaker 742 or the light emitting diode 740A or include the display of at least one status indication selected from the group consisting of a plurality of indications including when the next medicine is due, un-authorization of the user due to mismatching biometric characteristic and the like. Further configuration of the system 700 includes the status indication to be either in the form of display on the screen of the liquid crystal display unit 740, or the generation of beep from the speaker 742, or the light emitted from the light emitting diode 740A, or the vibration of the vibrator [not shown in the drawings] to indicate the current status of the system 700. The generation of beep varies with the status indication. The set of knobs 734, the liquid crystal display unit 740, speaker 742 and light emitting diode 740A are adapted and engineered in such a way to prevent the passage of air into the system 700 in order to protect the liquid medicine from the effect of moisture, except during the time of medicine dispense and at the time of refilling the enclosure 702 with a disposable liquid medicine dispensing unit 720A. The refilling includes the refilling of pre-determined liquid medicine. Further, in an additional aspect of the preferred embodiment of the present invention, the liquid crystal display unit 740 is configured to display the balance quantity of medicine available in the system 700 and further configured to display the due date of refilling the medicines into the system 700 wherein the refilling includes the replacement of the disposable liquid medicine dispensing unit 720A.

A communication facilitator 744 is provided in the system 700. The communication facilitator 744 is functionally coupled to the control unit 732. The communication facilitator 744 is preferably a two-way wireless communication device like modem connected to a remote server. The frequency and power level of radiation are chosen to be generic to medical devices to have least interference possible. The communication facilitator 744 enables the two-way communication between the system 700 and a remote server (not shown in the drawings) containing a plurality of medical records. The remote server (not shown in the drawings) enables a medical professional including but not limited to a physician and a pharmacist to receive a plurality of inputs including information on the usage pattern of medicine. The communication facilitator 744 is configured to function preferably in a low power local area network [LAN] to enable reduced frequency of recharging of the system 700. However, the communication facilitator 744 may also be configured to function in a high power wide area network [WAN]. Further, the two-way wireless communication device 744 is adapted to facilitate a medical professional including a physician and a pharmacist with the usage data to confirm authorized usage. The usage data is further used for exploratory analysis and statistical analysis and data extended analysis.

A threading pattern 710AA is designed at a point along the length of the lead pitch screw 710, beyond the mid-point and below the top-end 710A. There is provided a set of micro-leaf sensors 746A, 746B and 746C to facilitate the controlled movement of the piston-tail 720F and for control of replacement of the disposable liquid medicine receiving unit 720A. The first micro-leaf sensor 746A is positioned on the pin 716 below the piston-head 720G and the second micro-leaf sensor 746B is positioned near the bottom end of the pin 716 below the receiving unit 720. The third micro-leaf sensor 746C is below the sensor 746A with a small gap. The micro-leaf sensors 746A, 746B and 746C are functionally coupled to the control unit 732.

At the initial stage of operation of the system 700, the disposable liquid medicine dispensing unit 720A, full of liquid medicine is inserted inside the enclosure 702 by clockwise turning movement using suitable tool (not shown in drawing) to hold the disposable liquid medicine dispensing unit 720A. The threads on the disposable liquid medicine dispensing unit 720A meshes with the threading pattern 710AA of the system 700. When the edge of the disposable liquid medicine dispensing unit 720A near the piston-head 720G comes into contact with the first micro-leaf sensor 746A, the sensor 746A communicates a signal to the control unit 732. At the same time, the extended piston-tail 720F comes in contact with the disposable liquid medicine dispensing unit 720. Further, the nozzle tip 720C is covered with the nozzle cap 720D. Prior to the insertion of the disposable liquid medicine dispensing unit 720A inside the chamber 702, the receiving unit 720 comes to the bottom position of guide pin by the rotary movement of the stepper motor 722 and the receiving unit 720 comes into contact with the second micro-leaf sensor 746B. The second micro-leaf sensor 746B communicates a signal to the control unit 732 and the control unit in reply initiates a ready beep through the speaker 742 and a corresponding display at the liquid crystal display unit 740.

When the control unit 732 receives the signal from the first micro-leaf sensor 746A, it generates an audible beep through the speaker 742 and display through the liquid crystal display unit 740 to indicate full position is reached. On usage of liquid medicine, as the disposable liquid medicine dispensing unit 720 moves up, and when the disposable liquid medicine dispensing unit 720 comes in contact with the third micro-leaf sensor 746C, the third micro-leaf sensor 746C initiates a communication signal to the control unit 732 to indicate that liquid medicine end position is reached. An audible beep through the speaker 742 and corresponding display at the liquid crystal display unit 740 is generated to indicate that the liquid medicine end position is reached.

In all the aforementioned embodiments of the present invention, the system 100 as illustrated and described in FIG. 1, FIG. 2, FIG. 3, FIG. 3A, FIG. 4, FIG. 4A, FIG. 5, FIG. 5A, FIG. 6, FIG. 6A, FIG. 7, and the system 700 as illustrated and described in FIG. 8, may comprise additional enclosures identical to the enclosures 102 and 702 forming conjoined enclosure facilitating dispensing large amount of medicines and further facilitating longer duration of refilling the medicines.

A typical size for the system 100 and system 700 in all the aforementioned various embodiments of the present invention, to make it portable, compact and scale-down in size, is that the outer diameter and the length of the system 100 and system 700 would be about 1 inch and 7 inches respectively.

The system 100 and the system 700 in all the aforementioned embodiments of the present invention and illustrated and explained in accordance with the present invention, complies with the United States legislation for data privacy and security provisions for safeguarding medical information, pertaining to the rules and regulations provided under the Health Insurance Portability and Accountability Act of 1996 [HIPAA, enacted Aug. 21, 1996].

The various embodiments of the system 100 and the system 700 of the present invention is in compliance with a plurality of the internet of things [IoT] protocols via a plurality of service oriented software platforms which enable the plurality of personnel including but not limited to direct users of the system of the present invention, and authorized indirect users including but not limited to medical professionals and supply chain professionals, to have meaningful connectivity.

TECHNICAL ADVANTAGES AND ECONOMIC SIGNIFICANCE

The present invention provides a medicine dispensing system that:
  is tamper proof;
  is portable;
  is compact;
  is scaled-down in size;
  facilitates a user with controlled dispensing of medicines;
  facilitates control over misuse of medicines;
  enables dispensing pre-determined set of medicines at pre-determined time intervals;
  prevents the omission of the prescribed medication with respect to people suffering from mental health;
  enables authorized dispensing of medicines; and
  facilitates a medical professional including a physician or a pharmacist with the usage data that is further processed for exploratory data analysis and extended patient drug use analysis.

The embodiments of the present invention are particularly directed to address and overcome the drawbacks of the aforementioned prior art. While the present invention has been illustrated and described in detail with the figures and the description, such illustration and description are to be considered illustrative and exemplary only and not restrictive. The various embodiments and variations thereof as described herein and illustrated in the accompanying drawings are merely exemplary in nature and not mean to limit the spirit and scope of the invention. While the present invention has been disclosed in connection with the preferred embodiments, it will be understood that they are not intended to limit the present invention to these embodiments. On the contrary, the present invention is intended to cover all the amendments including modifications, alterations, changes and equivalents that may be considered within the spirit of the present invention and the scope of the appended claims. Therefore, those ordinarily skilled in the art will have no difficulty in devising and designing myriad obvious variations and improvements to the present invention. All these variations and improvements intended to be encompassed within the scope of the appended claims.

What is claimed is:

1. A compact portable scaled-down programmable stand-alone system for authorized dispensing of liquid medicines, comprising:

at least one enclosure having an open end, a closed end and a removable cap near the open end;

a disposable liquid medicine dispensing unit having a small nozzle with an orifice at the tip, a nozzle-cap adapted to cover said tip, a bottom end, a piston with a piston-tail proximate said bottom end and a piston-head adapted to carry and dispense a liquid medicine, said disposable liquid medicine dispensing unit contained in said enclosure;

a control unit adapted to facilitate controlled functioning of a plurality of functional units of said system;

a driving mechanism adapted to enable upward and downward movement of said piston associated with said disposable liquid medicine dispensing unit along the vertical length of said enclosure, said driving mechanism comprising a lead pitch screw having a top end and a bottom end, said lead pitch screw positioned adjacent to side wall of said enclosure below said removable cap and received through a set of screw-guides, a long pin positioned opposite and parallel to said lead pitch screw, said long pin received through a set of pin-guides, each said set of screw-guides and pin-guides mounted rigidly on the interior of said sidewall; a stepper motor fixed to the bottom-end of said lead pitch screw using a conveyor belt and a pair of first pulley and second pulley, and functionally coupled to said control unit wherein said first pulley coupled to the bottom-end of said lead pitch screw and said second pulley coupled to the shaft of said stepper motor, said conveyor belt configured to run over said pair of pulleys facilitating the upward and the downward movement of said piston;

at least one threading pattern configured at a point beyond the mid-point on the length of said lead pitch screw, a set of three micro-leaf sensors functionally coupled to said control unit and adapted to facilitate controlled movement of said piston-tail, said set of sensors further adapted to facilitate controlled replacement of said disposable liquid medicine dispensing unit, a first sensor of said micro-leaf sensor positioned on said long pin below said piston-head, a second sensor of said micro-leaf sensor positioned proximate the bottom end of said long pin and a third sensor of said micro-leaf sensor positioned below said first sensor with a distance of separation;

a primary sensor unit functionally coupled to said control unit and positioned near the closed end of said enclosure, said primary sensor unit adapted to facilitate identification and authorization of said user;

a power supply unit functionally coupled to said control unit and adapted to provide power supply for a plurality of operations;

a micro universal serial bus functionally coupled to said control unit, said micro universal serial bus adapted for electrical charging of said power supply unit and further adapted to enable external communication;

a global navigation satellite system module functionally coupled to said control unit and adapted to enable an authorized entity to locate the position of said system in a geography;

a set of status indicators comprising a liquid crystal display, a speaker, a vibrator and a light emitting diode, wherein each such liquid crystal display, speaker, vibrator and the light emitting diode functionally coupled to said control unit and adapted to generate at least one status of said system to alert said user;

a set of knobs functionally coupled to said control unit; and a communication facilitator functionally coupled to said control unit, said communication facilitator adapted to enable communication between said system and a remote server, said remote server adapted to enable a medical professional to receive a plurality of inputs including information on the usage pattern of liquid medicine, said communication facilitator adapted furthermore to function preferably in a low power local area network [LAN] to enable reduced frequency of recharging of said system, said system further configured to include a plurality of internet of things [IoT] modules.

2. The system of claim 1, wherein the structural material of said enclosure, and said disposable liquid medicine dispensing unit is a composite polymer.

3. The system of claim 1, wherein said primary sensor unit is a semiconductor based biometric sensor unit adapted to receive the fingerprint of said user.

4. The system of claim 1, wherein said external communication is selected from the group consisting of an external communication with said authorized user and an external communication with said remote server.

5. The system of claim 1, wherein said set of knobs, set of status indicators, and said removable cap adapted to guard said system with engineered sealing.

* * * * *